United States Patent [19]

Rösner et al.

[11] Patent Number: 4,640,917
[45] Date of Patent: Feb. 3, 1987

[54] 2-PHENYL-HEXAHYDRO-1,2,4-TRIAZINE-3,5-DIONES

[75] Inventors: Manfred Rösner, Eppstein; Wolfgang Raether, Dreieich, both of Fed. Rep. of Germany

[73] Assignee: Hoechst Aktiengesellschaft, Fed. Rep. of Germany

[21] Appl. No.: 709,798

[22] Filed: Mar. 8, 1985

[30] Foreign Application Priority Data

Mar. 12, 1984 [DE] Fed. Rep. of Germany ....... 3408924

[51] Int. Cl.⁴ .................. C07D 253/06; A61K 31/53; A61K 31/535; A61K 31/54
[52] U.S. Cl. ................................. 514/222; 514/227; 514/238; 514/242; 544/182; 544/112; 544/60; 544/83; 544/58.6
[58] Field of Search ............... 544/182, 112, 60, 58.6, 544/83; 514/222, 227, 238, 242

[56] References Cited

U.S. PATENT DOCUMENTS

| | | | |
|---|---|---|---|
| 3,560,496 | 2/1971 | Howes et al. | 544/182 |
| 3,655,891 | 4/1972 | Howes et al. | 424/249 |
| 3,905,971 | 9/1975 | Miller | 260/247.5 C |
| 3,912,723 | 10/1975 | Miller | 260/239.7 |
| 4,198,407 | 4/1980 | Rosner et al. | 544/182 |
| 4,426,522 | 1/1984 | Simonovitch | 544/182 |

FOREIGN PATENT DOCUMENTS

2606850  9/1977  Fed. Rep. of Germany .

OTHER PUBLICATIONS

Chem. Abs., 92:51708u, Miller et al., I (1980).
Chem. Abs., 95:180,651f, Miller et al., II (1981).
Chem. Abs., 88:152,571s, Minlibaeva et al., (1978).

*Primary Examiner*—John M. Ford
*Attorney, Agent, or Firm*—Finnegan, Henderson, Farabow, Garrett & Dunner

[57] ABSTRACT

Substituted 2-phenyl-hexahydro-1,2,4-triazine-3,5-diones of the formula

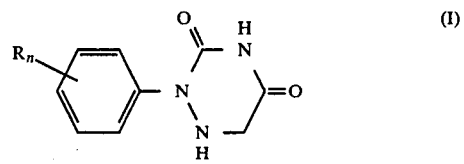

in which n is one, two or three and the individual substituents R are independently of one another (a) hydrogen, fluorine, chlorine, bromine, iodine, trifluoromethyl, alkyl having 1 to 6 carbon atoms, cycloalkyl having 3 to 6 carbon atoms, alkoxy, alkylthio, alkylsulfinyl or alkylsulfonyl each having 1 to 6 carbon atoms in the alkyl moiety, nitro, cyano, amino, alkylamino or dialkylamino each having 1 to 12 carbon atoms in the alkyl moiety, piperidino, morpholino, thiomorpholino, 1-pyrrolidinyl, 4-methyl-1-piperazinyl or acylamino having 1 to 6 carbon atoms in the acyl moiety, or (b) a phenoxy, phenylthio, phenylsulfinyl, phenylsulfonyl, benzoyl, benzoylamino or aniline radical which is in each case $R_{(a)}$-substituted, and the alkali metal salts, alkaline earth metal salts or ammonium salts thereof, a process for their preparation, their use, veterinary drugs and a process for controlling protozoal diseases.

6 Claims, No Drawings

2-PHENYL-HEXAHYDRO-1,2,4-TRIAZINE-3,5-DIONES

Coccidiostatically active 1,2,4-triazine-3,5-(2H,4H)-diones and their preparation have been disclosed, inter alia, by Belgian Pat. No. 740,403 and German Offenlegungsschriften No. 2,149,645, 2,423,972 and 2,722,537=U.S. Pat. No. 4,198,407. Hexahydro-1,2,4-triazine-3,5-diones with a benzyl- or thienylmethyl substituent in the 2-position have been described in European Patent Application No. 58,534.

The invention relates to novel substituted 2-phenyl-hexahydro-1,2,4-triazine-3-diones of the general formula I

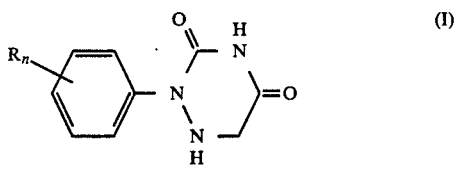

in which n is one, two or three and the individual substituents R are independently of one another (a) hydrogen, fluorine, chlorine, bromine, iodine, trifluoromethyl, alkyl having 1 to 6 carbon atoms, cycloalkyl having 3 to 6 carbon atoms, alkoxy alkylthio, alkylsulfinyl or alkylsulfonyl each having 1 to 6 carbon atoms in the alkyl moiety, nitro, cyano, amino, alkylamino or dialkylamino each having 1 to 12 carbon atoms in the alkyl moiety, piperidino, morpholino, thiomorpholino, 1-pyrrolidinyl, 4-methyl-1-piperazinyl or acylamino having 1 to 6 carbon atoms in the acyl moiety, or (b) a phenoxy, phenylthio, phenylsulfinyl, phenylsulfonyl, benzoyl, benzoylamino or aniline radical which is in each case $R_{(a)}$-substituted, and to the alkali metal salts, alkaline earth metal salts or ammonium salts thereof.

Those compounds of the formula I are preferred in which n is two or three and the individual substituents R are independently of one another (c) fluorine, chlorine, bromine, trifluoromethyl, alkyl having 1 to 6 carbon atoms, alkoxy, alkylthio or alkylsulfinyl each having 1 to 6 carbon atoms in the alkyl moiety, or (d) a phenoxy, phenylthio or phenylsulfinyl radical which is in each case $R_{(c)}$-substituted. Those compounds of the formula I are very particularly preferred in which n is two or three and the individual substituents R are independently of one another (e) chlorine, trifluoromethyl, alkyl having 1 to 4 carbon atoms, alkylthio or alkylsulfinyl each having 1 to 4 carbon atoms in the alkyl moiety, or (f) a phenoxy, phenylthio or phenylsulfinyl radical which is in each case $R_{(e)}$-substituted. Those compounds are also preferred in which the phenyl radical in the formula I is disubstituted in the 3,5-positions or trisubstituted in the 3,4,5-positions. In all the preferred compounds, the alkali metal salts, alkaline earth metal salts or ammonium salts are also included.

The invention also relates to the process for the preparation of substituted hexahydro-1,2,4-triazine-3,5-diones of the formula I, which comprises selectively hydrogenating a substituted 1,2,4-triazine-3,5-(2H,4H)-dione of the general formula II

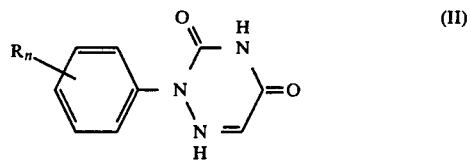

in which n and R are defined for the formula I, at the C—N— double bond.

The reduction can be carried out by conventional processes, such as are described, for example, in Houben-Weyl, Methoden der Organischen Chemie [Methods of Organic Chemistry], Volume 4/1c, pages 307 et seq., and Volume 4/1d, pages 365 et seq. Depending on the properties of the compound of the formula II, the reduction can be carried out, for example, by means of catalytically excited hydrogen with catalysts such as Raney nickel, platinum, palladium or platinum(IV) oxide, or by chemical reduction with metals, metal salts, metal carbonyls or complex hydrides. Sodium amalgam in ethanol, lithium in ammonia, tin(II) chloride in hydrochloric acid, iron in glacial acetic acid, lithium aluminum hydride, sodium borohydride and sodium cyanoborohydride may be mentioned as examples. Preferably, the reduction is carried out with zinc in glacial acetic acid or tin(II) chloride in hydrochloric acid, if appropriate in an inert solvent or diluent, such as methanol, ethanol, toluene, acetone, butanone, dimethoxyethane, tetrahydrofuran, dioxane, ethyl acetate, pyridine or glacial acetic acid. The reaction is in general carried out within a temperature range from about 50° C. to 150° C., preferably between 80° C. and 120° C., or at the boiling point of the solvent or solvent mixture used.

The processes for preparing compounds of the general formula II are known from the literature and are described, for example, in German Offenlegungsschrift No. 2,722,537=U.S. Pat. No. 4,198,407. They are prepared, for example by diazotization of an appropriately substituted aniline derivative and coupling of the diazonium salt with N,N'-bis-(ethoxycarbonyl)-malonic acid diamide, with subsequent cyclization, saponification and decarboxylation.

By the addition of advantageously one molar equivalent of an alkali, an alkaline earth or ammonia, the compounds of the formula I can be converted into the corresponding salts. Sodium hydroxide, sodium methylate, sodium hydride, potassium hydroxide, calcium hydroxide, calcium hydride or ammonia are preferably used for this purpose.

The compounds of the formula I, according to the invention, are novel chemotherapeutical agents, which can be used to combat protozoal diseases, and in particular as coccidiostatic agents. The compounds are also intermediates for the synthesis of medicaments.

In poultry rearing, coccidiosis causes mortality and hence large losses in terms of economics. For this reason, prophylactic and therapeutical measures are necessary. The emphasis is on prophylaxis, in particular on the administration of coccidiostatic agents in the fodder, preventing the outbreak of coccidiosis. In addition, these agents can also be used therapeutically in the case of already existing coccidiosis.

A coccidiostatic agent must have a high activity against various coccidia species at low use concentrations, good toleration and, resulting from this, a wide therapeutical range. In addition, novel coccidiostatic agents should be effective against coccidia strains which are already drug-resistant.

Even in very small quantities, the compounds of the formula I and their salts show a pronounced effect against various pathogens of coccidiosis in poultry and other animal species, coupled with very good toleration. Furthermore, they have an influence on coccidiosis pathogens which are resistant to several drugs.

The compounds of the formula I and their salts can in principle be administered as such in substance, in particular in the drinking water. Preferably, they are used as a mixture with a suitable carrier material.

The conventional fodder mixtures can be used as the carrier material. In this case, an active compound of the formula I is admixed to the fodder in a concentration of 0.1–300 ppm, preferably 0.5–50 ppm, in particular 0.5–30 ppm. As compared with the known aralkylhexahydrotriazines of European Patent Application No. 58,534, which are effective only within a range from 70 to 200 ppm in the fodder or drinking water, the compounds of the formula I, according to the invention, and their salts are distinguished in particular by the fact that they are effective even in substantially lower concentrations and at the same time show good toleration. It has been found that compounds of the formula I do not show any mutagenic effect in the Ames test.

EXAMPLES (1) 2-[3,5-Dichloro-4-(4-methylthio-phenoxy)-phenyl]-hexahydro-1,2,4-triazine-3,5-dione 20 g of 2-[3,5-dichloro-4-(4-methylthio-phenoxy)-phenyl]-1,2,4-triazine-3,5-(2H,4H)-dione were dissolved in 250 ml of hot glacial acetic acid. 30 g of zinc dust were added in portions, and the mixture was heated for 4 hours under reflux. The mixture was filtered off hot, the zinc-containing residue was boiled again repeatedly with glacial acetic acid and/or 2-methoxyethanol, and these solutions were filtered. The combined solutions were concentrated under reduced pressure and stirred into water. The resulting precipitate was filtered off with suction, washed with water, dried and recrystallized from glacial acetic acid or 2-methoxyethanol, if necessary with the addition of active charcoal. Melting point 239° C. (from 2-methoxy-ethanol).

NMR spectrum, 60 MHz, DMSO-d$_6$, TMS as internal standard, δ values in ppm: —NH—CH$_2$—3.7 d, J=8 Hz, and —NH—$\underline{CH_2}$—6.53 tr, J=8 Hz IR spectrum, $\overline{KBr}$: —NH—CH$_2$—3280 cm$^{-1}$, —NH—$\underline{CH_2}$ 2910 cm$^{-1}$, C=$\overline{O}$ 1680 and 1735 cm$^{-1}$ From the substituted 1,2,4-triazine-3,5-(2H,4H)-diones, the hexahydro-1,2,4-triazine-3,5-diones substituted in the same way were in each case obtained by reduction according to an analogous procedure:

Example 2: 2-[3,5-Dichloro-4-(4-methylsulfinyl-phenoxy)-phenyl]-hexahydro-1,2,4-triazine-3,5-dione, melting point 234°–235° C. (decomposition)

Example 3: 2-[3-Chloro-4-(4-methylthio-phenoxy)-phenyl]-hexahydro-1,2,4-triazine-3,5-dione, melting point 209° C.

Example 4: 2-[3,5-Dimethyl-4-(4-methylthio-phenoxy)-phenyl]-hexahydro-1,2,4-triazine-3,5-dione, melting point 193° C.

Example 5: 2-[4-(3-Methyl-4-methylthio-phenoxy)-phenyl]-hexahydro-1,2,4-triazine-3,5-dione, melting point 168° C.

Example 6: 2-[3,5-Dichloro-4-(3-methyl-4-methylthio-phenoxy)-phenyl]-hexahydro-1,2,4-triazine-3,5-dione, melting point 193° C.

Example 7: 2-(4-Phenylthio-phenyl)-hexahydro-1,2,4-triazine-3,5-dione, melting point 204°–205° C.

Example 8: 2-[3,5-Dichloro-4-(4-chlorophenylthio)-phenyl]-hexahydro-1,2,4-triazine-3,5-dione, melting point 247° C. decomposition Example 9: 2-[4-(4-Methylthio-phenylthio)-phenyl]-hexahydro-1,2,4-triazine-3,5-dione, melting point 222° C.

Example 10: 2-[3,5-Dichloro-4-(4-methylthio-phenylthio)-phenyl]-hexahydro-1,2,4-triazine-3,5-dione, melting point 237°–238° C.

Example 11: 2-(3,5-Dichloro-4-methylthio-phenyl)-hexahydro-1,2,4-triazine-3,5-dione, melting point 215°–216° C.

Example 12: 2-(3,5-Bistrifluoromethyl-phenyl)-hexahydro-1,2,4-triazine-3,5-dione, melting point 240° C.

(13) 2-[3,5-Dichloro-4-(4-methylthio-phenoxy)-phenyl]-hexahydro-1,2,4-triazine-3,5-dione 20 g of 2-[3,5-dichloro-4-(4-methylthio-phenoxy)-phenyl]-1,2,4-triazine-3,5-(2H,4H)-dione were dissolved in 200 ml of hot glacial acetic acid. 25 g of tin(II) chloride·2H$_2$O and then 100 ml of concentrated hydrochloric acid were added, and the mixture was subsequently heated for 4 hours under reflux. After cooling, the product was filtered off with suction, washed with water until neutral and recrystallized from 2-methoxyethanol; melting point 239° C.

From the substituted 1,2,4-triazine-3,5-(2H,4H)-diones, the hexahydro-1,2,4-triazine-b 3,5-diones substituted in the same way, of Examples 2 to 12, were obtained in each case by reduction, according to an analogous procedure.

EXAMPLE 14

2-[3,5-dichloro-4-(4-methylsulfonyl-phenoxy)phenyl]-hexyhydro-b 1,2,4-triazin-3,5-dione 10 g of 2-[3,5-dichloro-4-methylsulfonyl-phenoxy)-phenyl]-1,2,4-triazin-3,5-(2H,4H)-dione were dissolved in 150 ml of hot glacial acetic acid, 10 g of zinc dust were added, and the mixture was heated for two hours after reflux. The mixture was filtered off hot, the zinc-containing residue was boiled again three times with 50 ml glacial acetic acid. The combined solutions were concentrated under reduced pressure, then water was added and it was filtered off. The residue was recrystallized from methanol with the addition of active charcoal.

Melting point 240° C. with decomposition.

We claim:

1. A substituted 2-phenyl-hexahydro-1,2,4-triazine-3,5-dione of the formula

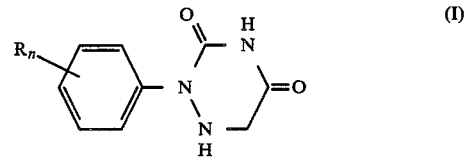

in which n is one, two or three and the individual substituents R are independently of one another (a) hydrogen, fluorine, chlorine, bromine, iodine, trifluoromethyl, alkyl having 1 to 6 carbon atoms, cycloalkyl having 3 to 6 carbon atoms, alkoxy, alkylthio, alkylsulfinyl or alkylsulfonyl each having 1 to 6 carbon atoms in the alkyl moiety, nitro, cyano, amino, alkylamino or dialkylamino each having 1 to 12 carbon atoms in the alkyl moiety, piperidino, morpholino, thiomorpholino, 1-pyrrolidinyl, 4-methyl-1-piperazinyl or acylamino having 1 to 6 carbon atoms in the acyl moiety, or (b) a phenoxy, phenylthio, phenylsulfinyl, phenylsulfonyl, benzoyl, benzoylamino or aniline radical which is in each case $R_{(a)}$-substituted, and the alkali metal salts, alkaline earth metal salts or ammonium salts thereof.

2. A compound of the formula I as claimed in claim 1, wherein n is two or three and the individual substituents R are independently of one another (c) fluorine, chlorine, bromine, trifluoromethyl, alkyl having 1 to 6 carbon atoms, alkoxy, alkylthio or alkylsulfinyl each having 1 to 6 carbon atoms in the alkyl moiety, or (d) a phenoxy, phenylthio or phenylsulfinyl radical which is in each case $R_{(c)}$-substituted, and the alkali metal salts, alkaline earth metal salts or ammonium salts thereof.

3. A compound of the formula I as claimed in claim 2, wherein n is two or three and the individual substituents R are independently of one another (e) chlorine, trifluoromethyl, alkyl having 1 to 4 carbon atoms, alkylthio or alkylsulfinyl each having 1 to 4 carbon atoms in the alkyl moiety, or a phenoxy, phenylthio or phenylsulfinyl radical which is in each case $R_{(e)}$-substituted, and the alkali metal salts, alkaline earth metal salts or ammonium salts thereof.

4. A compound of the formula I as claimed in claim 1, wherein n is two or three and the phenyl radical in the formula I is disubstituted in the 3,5-positions or trisubstituted in the 3,4,5-positions.

5. A veterinary drug, which comprises an effective amount of a compound of the formula I as claimed in claim 1, or said compound in admixture with a suitable carrier.

6. A process for controlling protozoal diseases, in particular coccidiosis, which comprises administering to an animal a fodder which contains an active compound of the formula I as claimed in claim 1, in a concentration of 0.1–300 ppm, preferably 0.5–50 ppm.

* * * * *